United States Patent [19]

Bernstein

[11] Patent Number: 4,704,355

[45] Date of Patent: Nov. 3, 1987

[54] ASSAY UTILIZING ATP ENCAPSULATED WITHIN LIPOSOME PARTICLES

[75] Inventor: David Bernstein, Sykesville, Md.

[73] Assignee: New Horizons Diagnostics Corporation, Columbia, Md.

[21] Appl. No.: 716,702

[22] Filed: Mar. 27, 1985

[51] Int. Cl.$^4$ .................... G01N 33/53; G01N 33/532
[52] U.S. Cl. ............................. 435/6; 435/8; 436/501; 436/520; 436/827; 436/829
[58] Field of Search ............... 436/520, 521, 827, 829, 436/501; 435/6, 8

[56] References Cited

U.S. PATENT DOCUMENTS

| | | | |
|---|---|---|---|
| 3,575,811 | 4/1971 | Chappelle | 435/8 |
| 3,850,578 | 11/1974 | McConnell . | |
| 4,014,745 | 3/1977 | Fletcher | 435/8 |
| 4,078,052 | 3/1978 | Papahadjopoulos . | |
| 4,193,983 | 3/1980 | Ullman et al. . | |
| 4,235,792 | 11/1980 | Hsia et al. . | |
| 4,235,871 | 11/1980 | Papahadjopoulos et al. . | |
| 4,241,046 | 12/1980 | Papahadjopoulos et al. . | |
| 4,246,340 | 1/1981 | Lundin et al. . | |
| 4,286,057 | 8/1981 | Wulff et al. . | |
| 4,298,685 | 11/1981 | Parikh | 435/7 |
| 4,314,026 | 2/1982 | Descamps et al. . | |
| 4,342,826 | 8/1982 | Cole . | |
| 4,358,535 | 11/1982 | Falkow | 435/35 X |
| 4,385,113 | 5/1983 | Chappelle et al. . | |
| 4,394,149 | 7/1983 | Szoka, Jr. et al. . | |
| 4,394,448 | 7/1983 | Szoka, Jr. et al. . | |
| 4,421,848 | 12/1983 | Whitlock | 435/8 |
| 4,429,008 | 1/1984 | Martin et al. . | |
| 4,480,041 | 10/1984 | Myles et al. . | |
| 4,483,929 | 11/1984 | Szoka | 435/8 X |
| 4,508,829 | 4/1985 | Sulitzeanu | 436/827 X |
| 4,581,222 | 4/1986 | Baldeschwieler | 436/827 X |
| 4,623,618 | 11/1986 | Rokugawa | 435/6 |

OTHER PUBLICATIONS

Chemical Abstracts, I, 100:47988b, (1984).
Chemical Abstracts, II, 91:189242y, (1979).
Chemical Abstracts, III, 94:170547s, (1981).
Endoh, H. et al., (1981), J. Immonol. Meth. 44:79-85.
DeLuca, M. et al., (1974), Biochem. 13:921-925.
Dunnick, J. K. et al., (1975), J. Nucl. Med., 16:483-487.
Huang, A. et al., (1980), J. Biol. Chem., 17:8015-8018.
Heath, T. D. et al., (1980), Biochim Biophys Acta, 599:42-62.
Papahadjopoulos, D. et al., (1967), Biochim Biophys Acta, 135:639-652.
Chowhan, Z. T. et al., (1972), Biochim Biophys Acta, 266:320-342.
Shen, D. F. et al., (1982), Biochim Biophys Acta, 689:31-37.
Heath, T. D. et al., (1981), Biochim Biophys Acta, 640:66-81.
Deamer, D. et al., (1976), Biochim Biophys Acta, 443:629-634.
Batzri, S. et al., (1973), Biochim Biophys Acta, 298:1015-1019.
Bangham, A. D., (1965), J. Mol. Biol., 13:238-252.
Huang, L. et al., (1979), Biochem, 18:1702-1707.
Uemura, K. et al., (1972), Biochem, 2:4085-4094.
Hastings et al., (1968), Ann Rev Biochem, 37:603.
Heath et al., (1980), Science, 210:539-541.

*Primary Examiner*—Sidney Marantz
*Attorney, Agent, or Firm*—Roylance, Abrams, Berdo & Goodman

[57] ABSTRACT

An assay utilizing receptor or antibody sensitized liposome particles which have ATP encapsulated therein. The ATP is released by lysing the liposomes, and detected by means of luciferin-luciferase reagent and a luminometer. The assay provides a very sensitive process for detecting the presence of analytes such as antigens and DNA probes.

19 Claims, No Drawings

ASSAY UTILIZING ATP ENCAPSULATED WITHIN LIPOSOME PARTICLES

FIELD OF THE INVENTION

This invention relates to biological assays. Specifically, the invention employs sensitized liposomes having ATP encapsulated therein for determining the presence of biological analytes such as antigens and DNA probes.

BACKGROUND OF THE INVENTION

Through recent innovations in the areas of instrumention, biological reagents, and high quality, inexpensive immunological reagents, it is now feasible to perform new types of immunoassays that were previously difficult or too costly. Additionally, recent advances in DNA probes and hybridization technologies have created a need for new amplification techniques which are nonradiactive and sensitive enough to detect a DNA (deoxyribonucleic acid) hybridization event.

In the clinical treatment and diagnosis of disease, it is advantageous to conduct testing in the physician's office or at a clinical laboratory where fast results are desirable. Instrumentation and reagent development have generally proceeded togeher, as exemplified by scintillation and gamma counters for radioimmunoassays, Elisa readers and spectrophotometers for enzymeimmunoassays and more recently fluorometers for fluorescent immunoassays. Inexpensive luminometers capable of reading light emissions from chemiluminescent and bioluminescent reactions, are now bringing these technologies toward commercial introduction for immunoassays. Accordingly, reagents which can be used with these inexpensive luminometers must also be developed.

Bioluminscent reactions such as the luciferin-luciferase reaction for the determination of adenosine triphosphate (ATP) make the detection of ATP one of the most sensitive luminescent reactions available. A significant number of publications exist in this area, illustrated by the following:

Deluca, M. (1976) *Advance in Enzymology* Vol. 44:37–68 John Wiley & Sons, N.Y. McElroy, W. D., Seliger, H. H. & Deluca (1974) *The Physiology of Insecta* Vol. 11:411–460, Academic Press, N.Y. These survey articles disclose that the reaction of luciferase, ATP and D-luciferin, produces free pyrophosphate and enzyme bound luciferyladenylate. The luciferyladenylate complex is subject to two processes which limit the speed of the initially emitted light, namely a conformational change and an abstraction of a proton from luciferyladenylate (DeLuca, M. & McElroy Biochem 13, 921–925, 1974). Luciferyladenylate is oxidized with oxygen under production of AMP and excited oxyluciferin, (which both remain enzyme bound), and carbon dioxide. Oxyluciferin is transformed to a ground state by emitting a photon. The energy for emitting the photon has been obtained from the oxidation of luciferin. Luciferin analogs make it possible to optimize the luciferin-luciferase ratio with respect to production cost of the reagent and increases stability of the light level.

U.S. Pat. No. 4,286,057 to Wulff discloses that the luciferase of the firefly (*Photinus pyralis* et al) catalyzes the following reaction;

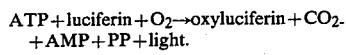

ATP+luciferin+$O_2$→oxyluciferin+$CO_2$+AMP+PP+light.

The light that is produced in this reaction is emitted with a yield of virtually 1 Einstein per mole of ATP, and has a wavelength of 562 nm at the peak. The reaction is extremely sensitive, and permits the quantitative determination of ATP concentration down to $10^{-13}$M per liter. This patent further teaches that the addition of AMP so modifies the properties of firefly luciferase, that the product inhibition by oxyluciferin, which usually occurs in the course of the reaction, is eliminated. The result is that, when a defined ATP concentration is measured, instead of the flash-like signal-time curve, a substantial constancy of signal over more than 15 minutes is achieved.

ATP determinations are based on a highly sensitive technique, resulting from the demonstration that luminescence in fireflies (Photinus pyralis) requires ATP and cannot use other sources of energy (Hastings J. W., Ann Rev Biochem 37:603, 1968). Light production with firefly lantern extract appears to be strictly proportional to the amount of ATP, and depends on the presence of luciferinluciferase, oxygen and magnesium ions. Under optimal conditions, each molecule of reacting ATP produces one photon of light. By means of present ultrasensitive photometers, this firefly bioluminescent reaction has now become the most sensitive method for ATP measurement.

In addition to ATP research, extensive work has been performed to stabilize and derivatize liposome particles as immunological reagents. The following publications are illustrative of this work:

U.S. Pat. No. 3,850,578 to McConnell discloses the use of sacs including erythrocyte ghosts, liposomes, or vesicles, which are lysable and capable of use in an immunoassay by containing an epitope on the surface of the sac which will be bound by its respective antibody. The antibody binding can occur through complement mediation resulting in lysis of the sac, or separation of agglutinated sacs followed by lysing of the sacs. The lysed sacs are loaded with a water soluble stable free radical compound, which can be detected when released into an environment external to the sac.

Kinsky et al, Biochemistry Vol. II, No. 22, 1972 pp. 4085–4093, describes the preparation and use of sensitized liposomes which are capable of being bound by specific antibodies and undergoing complement mediated immune lysis. Markers such as, for example, glucose entrapped in the liposomes are released and can be measured. The sensitizer is defined as the component which serves to render the liposome sensitive to lysis by a specific antiserum in the presence of complement. The sensitizer molecule comprises an amphiphilic body portion having a polar tail and a polar intermediate portion which is joined to an antigenic head.

Robinson, Trans. Faraday Soc. 56:1260–1264 (1960), and Papahadjopoulos et al Biochim. Biophys. Acta 135:639 (1967) describe a method of forming phospholipid dispersions from an ether-lipid aqueous two-phase system involving evaporation of the ether by bubbling nitrogen through the mixture.

Chowhan et al, Biophchim. Biophys. Acta, 266:320–342 (1972) describe a similar evaporation technique from a chloroform-aqueous two phase system using an excess aqueous phase and the slow removal of the chloroform phase in order to produce a uniform population of phospholipid vesicles.

Bangham et al J Mol Biol. 13:238–252 (1965) describes multilamellar lipid vesicles which could be characterized as having a small trapping volume, a low trapping efficiency (10%) and a confined aqueous space (15 to 35 A).

Batzri and Korr, Biochim. Biophys. Acta, 298:1015 (1973) using ethanol, and Deamer and Bangham Biochim. Biophys. Acta, 443:629–634 (1976) using ether, describe lipid vesicles prepared by injection of lipids in an organic phase into an aqueous solution. These methods produce unilamellar or paucilamellar vesicles.

U.S. Pat. No. 4,235,871 to Papahadjopoulos et al describes a method of encapsulating biologically active materials in synthetic, oligolamellar, lipid vesicles which comprises: providing a mixture of a vesicle wall forming compound in organic solvent and an aqueous mixture of the biologically active material to be encapsulated, the ratio of organic phase to aqueous phase being that which will produce an emulsion of the water-in-oil type; forming a homogeneous water-in-oil type of emulsion of said mixture; evaporating organic solvent from the emulsion, until a mixture is obtained having a gel-like character; and converting the gel-like mixture to a suspension of synthetic, oligolamellar vesicles encapsulating the biologically active material by one of the steps of (a) agitating said gel-like mixture and (b) dispersing said gel-like mixture in an aqueous media.

U.S. Pat. No. 4,429,008 to Martin et al describes a composition useful for conjugation with ligands bearing thiol groups, wherein each liposome has a lipid bilayer defining an outer surface for the liposome, and a plurality of thiol reactive groups integrally connected to the lipid bilayer and extending outward with respect to the outer surface.

Methods of associating antibodies with liposomes have been described and may be generally divided into two groups; nonspecific association and covalent attachment. Nonspecific association appears to rely upon the affinity of the Fc portion of the antibody for the hydrophobic region of the lipid bilayer.

Heath et al Science vol 210:539–541 (1980), reported efficiently covalently binding liposomes to biologically active proteins by periodate oxidation of glycosphingolipids.

SUMMARY OF THE INVENTION

Briefly, the invention comprises a process for assaying an analyte, said analyte being a member of a specific binding pair consisting of ligand and antiligand, wherein the process comprises the steps of: obtaining a first fluid suspected of containing the analyte to be determined; combining the first fluid with a solid support which has been sensitized with receptors that will bind the analyte to be determined; contacting the support with a second fluid comprising ATP encapsulated within the walls of liposomes, said liposomes having bonded thereto a compound which is either a ligand, ligand analog, or antiligand; and testing for the presence of ATP.

DETAILED DESCRIPTION OF THE INVENTION

Before considering the subject invention in detail, a number of terms used in the specification will be defined:

Antigen: any substance capable of provoking an immune response, particularly with the production of specific antibodies, in vertebrates. They include proteins, glycoproteins, glycolipids, polysaccharides, lipopolysaccharides.

Hapten: an incomplete antigen, incapable of itself in provoking an immune response, but when suitably attached to another molecule, generally a protein, becomes capable of producing antibodies which will specifically recognize the hapten molecule.

Epitope: a specific chemical and spacial configuration which is specifically recognized by an antibody. Antigens usually have a plurality of epitopic sites.

Analyte: the compound to be measured, which can be a ligand that is mono or polyepitopic, antigenic or haptenic, a single or plurality of compounds which share at least one common epitopic site or a receptor. The analyte can also be a DNA probe.

Ligand: any compound for which a receptor naturally exists or can be prepared.

Ligand analog: a modified ligand which can compete with the analogous ligand for a receptor, the modification providing means to join the modified ligand to another molecule.

Receptor: any compound capable of recognizing a particular spatial and polar organization of a molecule, i.e., epitopic site. They include antibodies, enzymes, antibody fragments such as Fab & Fab'2 fragments, DNA fragments, lectins, complement components, conglutinin, rheumatoid factors, hormones, avidin, staphylococcal protein 'A, etc.

DNA probe: small pieces of DNA that recognizes specific genes by hybridizing to complementary DNA.

Label (Marker): a compound which is either directly or indirectly involved with the production of a detectable signal.

Sac: a bag of any material enclosing a volume, having a wall composed of one or more components and having at least one internal compartment with the wall of the compartment forming a permeability barrier to the outside.

Vesicles: a term used to cover both single and multicompartmented sacs, but used herein solely to cover single compartment sacs.

Ghosts: sacs obtained from cells by removing cellular contents by opening the cellular membrane, either by physical or chemical means, so as to substantially empty the cell of its contents and then sealing the membrane, so as to enclose the material present in the sealing solution.

Liposomes: single or multicompartmented bodies obtained when lipids, particularly lipid mixtures, are dispersed in aqueous suspension. The walls or membranes are composed of a continuous lipid bilayer.

The high solubility and stability of ATP and the availability of inexpensive and stable luciferin-luciferase reagents provide an extremely sensitive method of identifying an immunological reaction of antigen or antibody coated liposome particles or a nucleic acid hybridization of a ligand-coupled DNA probe detected by antiligand-coated liposomes.

The presence of endogenous ATP in serum or urine samples and various inhibitors of the luciferin-luciferase reaction limits the reaction to a heterogeneous system, where immunologically bound liposomes must be separated from unbound liposomes. Fortunately there are a number of systems available to satisfy this requirement.

One such system is to use filtration, where the filtration membrane pore size is large enough to allow unbound liposomes to flow freely upon vacuum or pressure, but retains bound liposomes to larger particles which are also immunologically tagged.

For example, in an assay for detection of a multivalent analyte, the sample fluid (serum, plasma, urine, saliva, etc.) is incubated with large size beads which have been sensitized with antibody, lectins, or other receptors that bind the particular analyte in question. After a suitable incubation period, the reactants are filtered through a membrane and washed in a suitable buffer. The ATP laden liposomes which have been conjugated to a specific antibody or receptor to the analyte in question are then brought in contact with the test particles and incubated for a suitable period. The mixture is again filtered and washed in a suitable buffer. The entrapped bound liposomes are then reacted with a releasing reagent such as saponin. The released ATP is then quantified in an assay utilizing luciferin-luciferase reagent, and the resulting light emission is determined in a photometer (luminometer). In this example, the presence of the analyte would be indicated by a significant presence of ATP.

Another option for use of ATP laden immunologically reactive liposomes would involve using them in a heterogeneous assay on strips or membranes which have entrapped or bound thereon the analyte of interest. The liposomes can be reacted with these strips, and after washing, the bound liposomes could be lysed and the released ATP measured in a luciferin-luciferase ATP assay.

In the case where the analyte is a DNA probe, the assay would be as follows: The DNA probe is tagged with a ligand such as biotinylated modified nucleotide. A hybridization with complementary DNA is allowed to occur and is immobilized on a support such as a membrane or particle. After suitable washing, the bound probe is reacted with ATP laden liposomes sensitized with a receptor to the ligand. The receptor can be adsorbed or covalently attached to the liposomes. In the case where the DNA probe is biotinylated, the receptor is avidin. The reactants are subsequently washed and the amount of ATP in the bound liposomes is determined.

Instead of biotin and avidin, other ligand/antiligand compounds may be used such as fluorescein and antifluorescein, a hapten and an antibody specific to the hapten, or a lectin and sugar moiety-containing compound which will bind to said lectin.

The liposomes can be used with antigens covalently attached or absorbed, or with ligands such as staphylococcal protein A, specific antibody to Fc fragment portions of immunoglobulins, avidin for binding to biotinylated antibodies or DNA probes, conglutinin or rheumatoid factors for binding to immune complexes, etc.

The assays can be competitive inhibition assays where the analyte is a univalent hapten or molecule. For example, in an assay for detecting heroin, a morphine protein conjugate can be coupled to liposome reagent. Specific antimorphine antibody can be covalently attached to the capture particles. The capture particles are reacted with the test sample (urine) and after a suitable incubation are filtered and washed. The liposome with morphine conjugate reagent is then added and incubated with the capture beads. After a suitable time, the particles are filtered, washed and the amount of binding of liposomes is determined as above. The decrease or inhibition of binding liposomes compared to a standard curve is demonstrative of the presence of morphine in the sample. In other words, the presence of morphine would be indicated by the relative absence of ATP.

In another embodiment of the invention, liposome particles can be coupled to a second antibody reagent or receptor, (i.e., anti mouse Fc, avidin, etc.). In detection of bacterial antigens or viral antigens, the capture particles are sensitized with specific antibody or lectin to specific epitopes of the antigen and reacted with the sample (an extract of the test specimen, generally an exudate, purulant discharge or vesicle fluid, etc.) and a specific antibody which recognizes another epitope of the antigen. After suitable incubation, the reactants are filtered, washed and a complimentary matched liposome for the free specific antibody or receptor is used as the marker. For example, if the capture material on the bead is a non-immunoglobulin such as a lectin, then the second antibody could be an immunoglobulin in which case the liposome uses an antibody capable of recognizing that species of immunoglobulin, or a protein such as staphylococcal protein A which binds to certain immunoglobulins. If the capture material on the bead is an immunoglobulin, then the second antibody used should be either from another species of animal or a biotinylated antibody. The liposome would be coupled with antibody to case of the biotinylated antibody, the liposome would be coupled to avidin.

In this invention, liposomes may be prepared by any of various conventional methods to produce either unilamellar vesicles or multilamellar vesicles. The liposomes are synthetic lipid vesicles prepared by suspending lipid films in an aqueous media containing a high concentration of the molecule adenosine triphosphate. The liposomes are prepared with either antigen epitopes or antibody covalently or non-covalently attached to their surfaces.

In one method, lipids are physically dispersed into an aqueous solution, and a dry thin film of lipids is formed on the interior surface of a suitable vessel. The aqueous solution containing the substances to be entrapped within the liposomes is then placed in the vessel in contact with the lipid film. The lipid film is then dispersed in the aqueous solution by vigorous agitation.

Alternatively, lipids may be dissolved in an aqueous solution containing a detergent such as sodium dodecylsulfate, sodium deoxycholate, or Triton X 100, which is the tradename for a nonionic detergent produced by a Rohm and Haas. The detergent is then removed and the liposome bilayers are formed.

Another known technique involves the addition of an aqueous solution containing lipids to a volatile organic solvent. The solvent is subsequently removed by evaporation at reduced pressure.

Liposomes with very large internal aqueous space can be prepared by evaporating organic solvents such as diethyl ether or isopropyl ether.

After the liposomes have been formed, antigens may be covalently bonded or in some cases absorbed to the surface. Alternatively, the antigen may be covalently coupled to an appropriate amphiphile and this complex included in the lipid mixture from which the liposomes are formed. When liposomes are preformed, they can have at their external surface several chemical functionalities to which antigens may be covalently attached. Amino groups derived from phosphatidyl ethanolamine, hydroxyl groups provided by phosphatidyl inositol, and carboxyl groups provided by fatty acids or phosphatidyl serine. Antigens may be coupled using bifunctional coupling agents such as: glutaraldehyde, bis p-nitrophenyl esters of dicarboxylic acid, aromatic disulfonyl chlorides and bifunctional arylhalides such as 1,5 difluoro-2,4-dinitrobenzene and p,p-difluoro -m,m -dinitro-diphenylsufone. Also diimide esters, aromatic and aliphatic diisocyanates, metamaleimidobenzoyl n-hydroxysuccinimide, (MBS), or n-gamma-maleimidobutyryl-oxysuccinimide (GMBS).

Endogenous complement activity can be prevented by the addition of the sulfonic acid azo dye "chlorazol fast pink" which inhibits human complement, or the serum can be heated before use for 30 to 60 minutes at 58° C.

There are a number of approaches to binding antibody to liposomes as illustrated by the following references which are expressly incorporated herein:

Magee and Miller, Nature 235:339-341 (1972), describe rehydrating dried lipid films in the presence of antibody preparations. The antibody becomes liposome associated through a combination of hydrophobic and ionic interactions.

Huang and Kennel, Biochemistry 18:1702-1707 (1979), describe the co-sonication of multilamellar vesicles with antibodies. The extent of binding increases by the inclusion in the phosphatidylcholine liposomes of anionic phospholipids and depends on the time and power intensity of sonication.

Published reports by Heath et al Biochim. Biophys. Acta 599:42-62 (1980); Martin et a Biochemistry 20:4229-4238 (1981); and Dunnick et al J. Nucl. Med. 16:483-487 (1975), describe methods for covalently coupling proteins to functional groups on the liposome surface or attaching a hydrophobic residue covalently to the proteins and allowing them to intercalate non-covalently into the bilayer during or after the liposome formation. See also Huang et al, J. Biol. Chem. 255:8015-8018, (1980).

Heath et al, Biochim. Biophys. Acta, 599:42-62 (1980); and 640:66-81 (1981) used periodate to oxidize bilayer situated glycosphingolipids, thereby generating a reactive aldehyde moiety in the liposome capable of binding to free amino groups of protein. Others have used SPDP derivated phosphatidyl ethanolamine which can be inserted in the bilayer of the liposome and incubated with rabbit Fab' fragments at pH 8.0 under inert atmosphere.

Coupling of antibodies can also be accomplished by use of water soluble cross-linking reagent 1-ethyl-3, 3-dimethylaminopropyl carbodiimide (EDCI), as reported by Endoh et al, J. Immunol. Meth. 44:79-85, (1981). The fixation of antibody, either by EDCI mediated coupling or by adsorption, on the surface of the liposomal membrane reduces the activity of complement dependent cytolysis, probably because of inactivation of the Fc part of the molecule.

Shen et al Biochim. Biophys. Act 689:31-37, (1982) describe a method of coupling monoclonal antibody to palmitic acid and incorporating this conjugate into liposomes by reverse phase evaporation methods. Palmitoyl antibody in 0.15% deoxycholate is added to a lipsome suspension after the majority of the organic solvent has been removed by evaporation. Efficient incorporation, over 80%, of palmitoyl antibody occurs without leakage of the encapsulated drug.

EXAMPLE 1

Synthesis of PDP-DPPE

N-succinimidyl 3-(2-pyridyldithio) propionate (SPDP) 75 mg, was dissolved in 9.0 millimeters of anhydrous methanol under nitrogen. Twenty one microliters of triethylamine was added. L alpha-dipalmitoylphosphatidylethanolamine, 104 mg, dissolved in 14.2 milliliters of chloroform was added to the SPDP solution and reacted for 18 hours at room temperature. The reactants were placed in a rotoevaporator and the chloroform-methanol was evaporated at 44 degrees centigrade. Nine milliliters of fresh chloroform was added to the flask, followed by the addition of 9.0 millimeters of 0.01M phosphate buffered saline, pH 7.3, and mixed. The mixture was transferred to a separatory funnel and the aqueous phase was removed and discarded. The organic phase was washed again with phosphate buffered saline followed by distilled water. The organic phase (20 milliliters) was dried with calcium chloride, filtered and placed on a 100 ml silica gel column equilibrated in chloroform. The column was washed with 300 ml chloroform:methanol (10:1) and eluted with 300 ml. chloroform:methanol (5:1). The eluted fraction was concentrated under vacuum to 10.0 milliliters and found to contain $3.3 \times 10^{-3}$ moles/liter N-3-(2-pyridyldithiopropionyl)-dipalmitoylphosphatidylethanolamine (PDP-DPPE).

Preparation of ATP Marker

Two hundred milligrams of adenosine 5'-triphosphate disodium salt (ATP), and 7.4 milligrams of ethylenedinitrotetraacetate disodium salt (EDTA) were dissolved in water and the pH adjusted to 8.0 with IN NaOH. The solution was then adjusted to a final volume of 20.0 milliliters with water with a final concentration of ATP at 1.0% (w/v).

Preparation of ATP Loaded Liposomes

L alpha-dipalmitoylphosphatidylcholine (DPPC), 48.4 milligrams, 6.0 milligrams of PDP-DPPE, and 255.0 mg cholesterol were combined, followed by the addition of 1.1 milliliters chloroform, 3.0 milliliters diethyl ether, 0.5 milliliters anhydrous methanol and 2.0 milliliters ATP marker solution. The reactants were vigorously shaken under nitrogen and an additional 10.0 milliliters of ATP marker solution was added. The mixture was rotated on a rotoevaporator at 44° C. The liposomes were then dialyzed extensively against 1 liter of 0.50M TRIS buffer containing 0.001M EDTA, and 0.340M sodium chloride, pH 8.0, with four changes of dialyzing buffer.

Preparation of Fab' Fragments

Affinity purified rabbit anti Group A streptococcal antibody was digested with pepsin at pH 4.5 for 18 hours at room temperature. The Fab'$_2$ fragments were separated on a G-25 sephadex column. Fab'$_2$ fragments (1.7 mg) were reacted with 0.02 mM dithiothreitol (DTT) and separated on a G-25 column equilibrated with 50 mM TRIS containing 340 mM sodium chloride, 1 mM EDTA, pH 6.0. The protein peak in the void volumn of the column contained 850 ug/ml protein.

Coupling of Fab' to PDP-Liposomes

Fab' (170 micrograms) was reacted for 18 hours at 4° under nitrogen with 1.5 ml of the dialyzed PDP-liposomes. Without any further treatment, the Fab'-coupled liposomes were diluted in 0.1% BSA, 50 mM TRIS, 340 mM sodium chloride, 1 mM EDTA, 0.02% sodium azide, pH 8.0.

Testing of ATP Loaded Anti Strep Group A
Liposomes Using Sandwich Assay on a PVC Plate 1. A polyvinylchloride ELISA plate was precoated with rabbit anti Group A streptococci antibody in 0.05M carbonate-bicarbonate buffer pH 9.5 for 18 hours at 4° C., then blocked with 1% BSA, then washed with 0.05M phosphate buffered saline, and 0.05% Triton X-100, pH 7.5.
2. Fifty microliters of dilutions of nitrous acid extracts of Group A and Group C streptococci were reacted for 30 minutes in the ELISA plate. The plate was then washed with the PBS-triton buffer.
3. Fifty microliters of a 1:25 dilution of anti strep Group A liposomes were added to each well and incubated for 30 minutes at room temperature. The plate was then washed with PBS Triton X buffer.
4. Fifty microliters of ATP releasing reagent (saponin detergent) was added to each well and then reacted with fifty microliters of a luciferin-luciferase reagent.
5. The light emitted was read in a luminometer.

| DILUTION OF CARBOHYDRATE (CHO) | Light Units Emitted/Min | |
|---|---|---|
| | A CHO | C CHO |
| $10^{-2}$ | 15,384 | 389 |
| $10^{-3}$ | 17,976 | 459 |
| $10^{-4}$ | 7,552 | 587 |
| $10^{-5}$ | 1,492 | 417 |
| $10^{-6}$ | 556 | 458 |

The presence of Group A strep is indicated by the higher light emission of the Group A infected sample. This corresponds to the significant presence of ATP.

EXAMPLE 2

The procedure of Example 1 was followed for preparing the Fab' fragments, and coupling of Fab' to PDP-Liposomes. A filtration assay using capture particles was then performed as follows:
1. One hundred microliters of anti Group A strep or control rabbit immunoglobulin-coupled polystyrene particles (0.25%) were added to a 0.22 microfiltration tray.
2. Fifty microliters of Group A carbohydrate dilutions were added and incubated for 30 minutes at room temperature.
3. The particles were washed in the plate with 0.05M phosphate buffered saline, pH 7.5, containing 0.05% Triton X-100 under vacuum pressure.
4. Fifty microliters of strep liposomes were added and incubated for 30 minutes at room temperature.
5. The particles were washed again in the same PBS Triton buffer.
6. One hundred microliters of releasing reagent (saponin) were added to each well.
7. Fifty microliters of released ATP were added to a cuvette and fifty microliters of luciferin-luciferase reagent were added.
8. The light emitted was read in a luminometer.

| DILUTION OF CARBOHYDRATE | Light Units Emitted/Min | |
|---|---|---|
| | Anti Gp A | Control |
| $10^{-2}$ | 32,565 | 5868 |
| $10^{-3}$ | 23,235 | 5333 |
| $10^{-4}$ | 10,275 | 5243 |
| $10^{-5}$ | 7,555 | 3224 |
| $10^{-6}$ | 6,141 | 3003 |
| $10^{-7}$ | 5,696 | 4004 |

The presence of Group A strep antigen is indicated by the significant presence of ATP, evidenced by significantly greater light emission of the Group A strep sample than the control, especially at low dilution.

EXAMPLE 3

The procedure of Example 1 was followed for preparing the Fab' fragments, and coupling of Fab' to PDP-liposomes. A rapid immunoassay using capture particles and centrifugation was then performed as follows:
1. One hundred microliters of anti Group A Strep-coupled polystyrene particles (0.25%) were reacted with fifty microliters of Group A or Group C streptococcal extract dilutions, and fifty microliters of anti Group A liposomes (1:5) in microfuge tubes. The reactants were vortexed and incubated for twenty minutes at room temperature.
2. The reactants were centrifuged and washed with PBS Triton buffer.
3. Fifty microliters of releasing reagent were added and mixed with fifty microliters of luciferin-luciferase ragent.
4. The light emitted was read in a luminometer.

| DILUTION OF CARBOHYDRATE | Light Units Emitted/Min | |
|---|---|---|
| | Gp A CHO | Gp C CHO |
| $10^{-2}$ | 15,032 | 1415 |
| $10^{-3}$ | 6,888 | 1517 |
| $10^{-4}$ | 2,558 | 1277 |
| $10^{-5}$ | 2,605 | 1707 |
| Buffer | 1179 | |

Again, the presence of Group A strep is indicated by the significant presence of ATP, manifested by the significantly greater light emission by the Group A strep sample.

What is claimed is:

1. A process for assaying an analyte, said analyte being a member of a specific binding pair selected from the group consisting of ligand and antiligand, wherein said process comprises the steps of:
   obtaining a first fluid suspected of containing the analyte to be determined,
   combining the first fluid with a solid support, said support having been sensitized with receptors that will bind the analyte to be determined,
   contacting the support with a second fluid comprising ATP encapsulated within the walls of liposomes, said liposomes having bonded thereto a compound, wherein said compound is ligand, ligand analog, or antiligand, and
   testing for the presence of ATP associated with the support.
2. The process of claim 1, wherein
   the step of testing for the presence of ATP includes the steps of:
   contacting the solid support and bound immunological particles thereon with a reagent capable of releasing the ATP from the liposomes, mixing the released ATP with luciferin-luciferase reagent, and determining the amount of released ATP by means of a luminometer.

3. The process of claim 1, further including the steps of washing the substrate before and after contact with the second fluid.

4. The process of claim 1, wherein the solid support is a bead.

5. The process of claim 1, wherein the solid support is a strip.

6. The process of claim 1, wherein the solid support is a membrane.

7. The process of claim 1, wherein said analyte is a DNA probe.

8. The process of claim 1, wherein the compound bonded to the liposome is capable of binding the analyte.

9. The process of claim 8, wherein upon testing, the presence of analyte is indicated by a significant presence of ATP.

10. The process of claim 8 further including the step of prior to said testing for ATP, filtering said second fluid to remove liposomes which do not bind to said analyte.

11. The process of claim 1, wherein the compound bonded to the liposome is capable of binding to the receptors on the solid support.

12. The process of claim 11, wherein upon testing, the presence of analyte is indicated by the relative absence of ATP.

13. The process of claim 11, further including the step of prior to said testing for ATP, filtering said second fluid to remove liposomes which do not bind to the receptors.

14. A process for determining the presence of hybridized DNA comprising the steps of:

providing a first fluid comprising at least one DNA probe, said DNA probe having bonded thereto a first compound, wherein said first compound is ligand, ligand analog, or antiligand, combining said first fluid with a second fluid suspected of containing complementary DNA, said complementary DNA is complementary to said at least one DNA probe.

immobilizing, on a support, any hybridized DNA formed from combining said first fluid with said second fluid, contacting said support and said any immobilized hybridized DNA with a third fluid comprising ATP encapsulated within the walls of lipsomes, said liposomes having bonded thereto a second compound, said second compound is a ligand, ligand analog, or antiligand, which is capable of binding said first compound, and testing for the presence of ATP associated with the support.

15. The process of claim 14, wherein the step of testing for the presence of ATP includes the steps of:

contacting the solid support and said any immobilized hybridized DNA with a reagent capable of releasing the ATP from liposomes, mixing the released ATP with luciferin-luciferase reagent, and determining the amount of released ATP by means of a luminometer.

16. The process of claim 14, wherein said first and second compounds are biotin and avidin.

17. The process of claim 14, wherein said first and second compounds are fluorescein and antifluorescein.

18. The process of claim 14, wherein said first and second compounds are a hapten and an antibody specific to said hapten.

19. The process of claim 14, wherein said first and second compounds are a lectin and a sugar moiety-containing compound which will bind to said lectin.

* * * * *